United States Patent
Soza et al.

(10) Patent No.: US 11,850,086 B2
(45) Date of Patent: Dec. 26, 2023

(54) METHOD AND CONTROL FACILITY FOR CONTROLLING A MEDICAL IMAGING SYSTEM

(71) Applicant: Siemens Healthcare GmbH, Erlangen (DE)

(72) Inventors: Grzegorz Soza, Heroldsberg (DE); Michael Suehling, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 956 days.

(21) Appl. No.: 16/114,314

(22) Filed: Aug. 28, 2018

(65) Prior Publication Data
US 2019/0069869 A1 Mar. 7, 2019

(30) Foreign Application Priority Data
Sep. 1, 2017 (EP) ..................... 17188953

(51) Int. Cl.
*A61B 6/00* (2006.01)
*A61B 6/03* (2006.01)
(Continued)

(52) U.S. Cl.
CPC .............. *A61B 6/545* (2013.01); *A61B 6/032* (2013.01); *A61B 6/4447* (2013.01);
(Continued)

(58) Field of Classification Search
CPC ....... A61B 6/545; A61B 6/4447; A61B 6/032; A61B 6/481; A61B 6/503; A61B 6/54;
(Continued)

(56) References Cited

U.S. PATENT DOCUMENTS

2005/0121505 A1 6/2005 Metz et al.
2005/0267348 A1* 12/2005 Wollenweber ......... A61B 6/544
600/407
(Continued)

FOREIGN PATENT DOCUMENTS

CN 104487974 A 4/2015
DE 102016213515 A1 1/2016
(Continued)

OTHER PUBLICATIONS

European Office Action dated Nov. 9, 2020.
(Continued)

*Primary Examiner* — Eliza A Lam
(74) *Attorney, Agent, or Firm* — Harness, Dickey & Pierce, P.L.C.

(57) ABSTRACT

A method is for controlling a medical imaging system. The method includes providing a data record for a patient, the data record including indication data; mapping at least the indication data into an ontology; providing a control data library including control data records for at least one medical imaging system; automatically determining a control data record from the control data library as a function of the at least indication data mapped into the ontology, via at least one of an inference and numerical modeling; and controlling the medical imaging system with the control data record automatically determined. Furthermore, a related control facility and a medical imaging system are also disclosed.

26 Claims, 3 Drawing Sheets

(51) Int. Cl.
  *G16H 40/63* (2018.01)
  *G16H 50/70* (2018.01)
  *G06F 16/28* (2019.01)
  *G16H 30/40* (2018.01)
  *G16H 10/60* (2018.01)
  *G16H 30/20* (2018.01)

(52) U.S. Cl.
  CPC .......... *G06F 16/285* (2019.01); *G16H 40/63* (2018.01); *G16H 50/70* (2018.01); *G16H 10/60* (2018.01); *G16H 30/20* (2018.01); *G16H 30/40* (2018.01)

(58) Field of Classification Search
  CPC ........ G16H 50/70; G16H 40/63; G16H 30/40; G16H 10/60; G16H 30/20; G06F 16/285
  See application file for complete search history.

(56) References Cited

U.S. PATENT DOCUMENTS

2008/0109250 A1* 5/2008 Walker .................. G16H 15/00
  715/255
2008/0172249 A1 7/2008 Glaser-Seidnitzer et al.
2017/0323442 A1 11/2017 Suehling et al.

FOREIGN PATENT DOCUMENTS

JP        2015524107 A  *  8/2015  ............. G16H 10/60
WO    WO 2012104786 A2    8/2012
WO    WO 2013179216 A2    12/2013

OTHER PUBLICATIONS

Spanier, A. B. et al. "A new method for the automatic retrieval of medical cases based on the RadLex ontology", International Journal of Computer Assisted Radiology and Surgery, Springer, DE, vol. 12, NR. 3, pp. 471-484, XP036159446. ISSN: 1861-6410, DOI: 10.1007/S11548-016-1496-Y.
Extended European Search Report #17188953.8 dated Mar. 22, 2018.

* cited by examiner

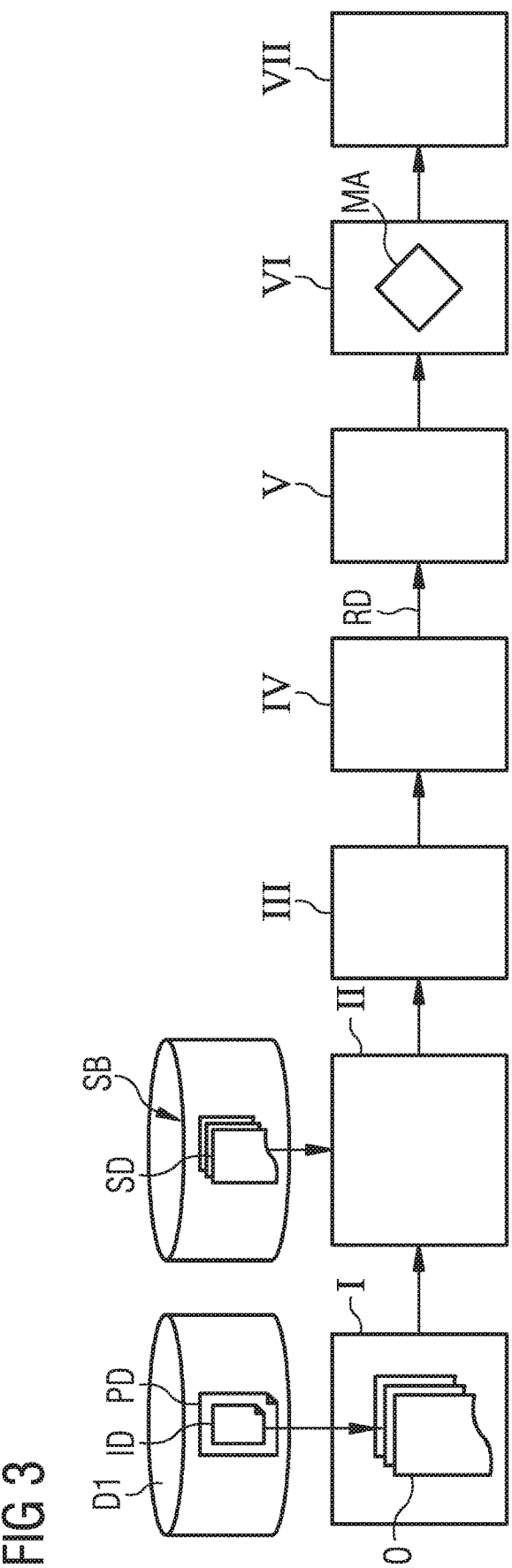

METHOD AND CONTROL FACILITY FOR CONTROLLING A MEDICAL IMAGING SYSTEM

PRIORITY STATEMENT

The present application hereby claims priority under 35 U.S.C. § 119 to European patent application number EP17188953.8 filed Sep. 1, 2017, the entire contents of which are hereby incorporated herein by reference.

FIELD

At least one embodiment of the invention generally relates to a method and a control facility for controlling a medical imaging system, as well as to a medical imaging system controlled in such a manner.

BACKGROUND

The optimal acquisition and reconstruction of CT scans is a fundamental step in order to achieve a high-quality diagnosis result.

In current clinical work, both the selection of scan protocols and contrast protocols and also the rules for the image reconstruction thereof are carried out on the basis of manually defined configuration rules. These manually defined configuration rules depend upon the information from radiological information systems or are performed by a technician in the examination room completely manually for each individual patient at the point of image recording. Information regarding current and further patients, a clinical history or clinical reports is currently not used at all. Thus, the scanning and reconstructing process is the same in each case for each patient with the same clinical indication, at least provided that no manual settings are carried out at the medical device in question.

This is disadvantageous, since such an approach is very time-consuming and an individual setting for each patient to be examined is hardly practicable.

SUMMARY

At least one embodiment of the present invention makes available an improved method and a correspondingly improved control facility, with which at least one the disadvantages described above are reduced and/or avoided.

Embodiments are directed to a method, a control facility, and a medical imaging system.

At least one embodiment of a method according to the application, for controlling a medical imaging system, in particular for automatically determining control commands for such a system, comprises:
  providing a data record for a patient, containing indication data;
  mapping at least the indication data into an ontology;
  providing a control data library comprising control data records for at least one medical imaging system;
  automatically determining a control data record from the control data library as a function of the indication data mapped into the ontology, by way of an inference and/or numerical modeling; and
  controlling the medical imaging system with the determined control data record.

At least one embodiment of the application is directed to a control facility control facility, for controlling a medical imaging system, comprising
  an interface for providing a data record of a patient, containing indication data;
  an interface and/or a database for providing a control data library comprising control data records for at least one medical imaging system;
  a transfer unit configured for transferring at least the indication data into an ontology; and
  a determination unit, configured for determining a control data record from the control data library as a function of the indication data mapped into the ontology, by way of a semantic inference and/or numerical modeling.

At least one embodiment of the application is directed to a medical imaging system comprising a control facility of an embodiment of the application.

At least one embodiment of the application is directed to a computer program product storing a computer program which can be loaded directly into a memory store of a control facility of a medical imaging system, having program portions in order to carry out the method of an embodiment of the application when the computer program is executed in the control device.

At least one embodiment of the application is directed to a computer-readable medium storing program portions that can be read in and executed by a computer unit, in order to carry out the method of an embodiment of the application when the program portions are executed by the computer unit.

BRIEF DESCRIPTION OF THE DRAWINGS

The invention will be described again in greater detail below using example embodiments by reference to the accompanying drawings. In the various drawings, the same components are identified with identical reference signs. The figures are generally not shown true to scale, in which:
FIG. 3 shows a block diagram for clarifying the sequence of a preferred embodiment of the method according to the invention.

DETAILED DESCRIPTION OF THE EXAMPLE EMBODIMENTS

Figure 1:
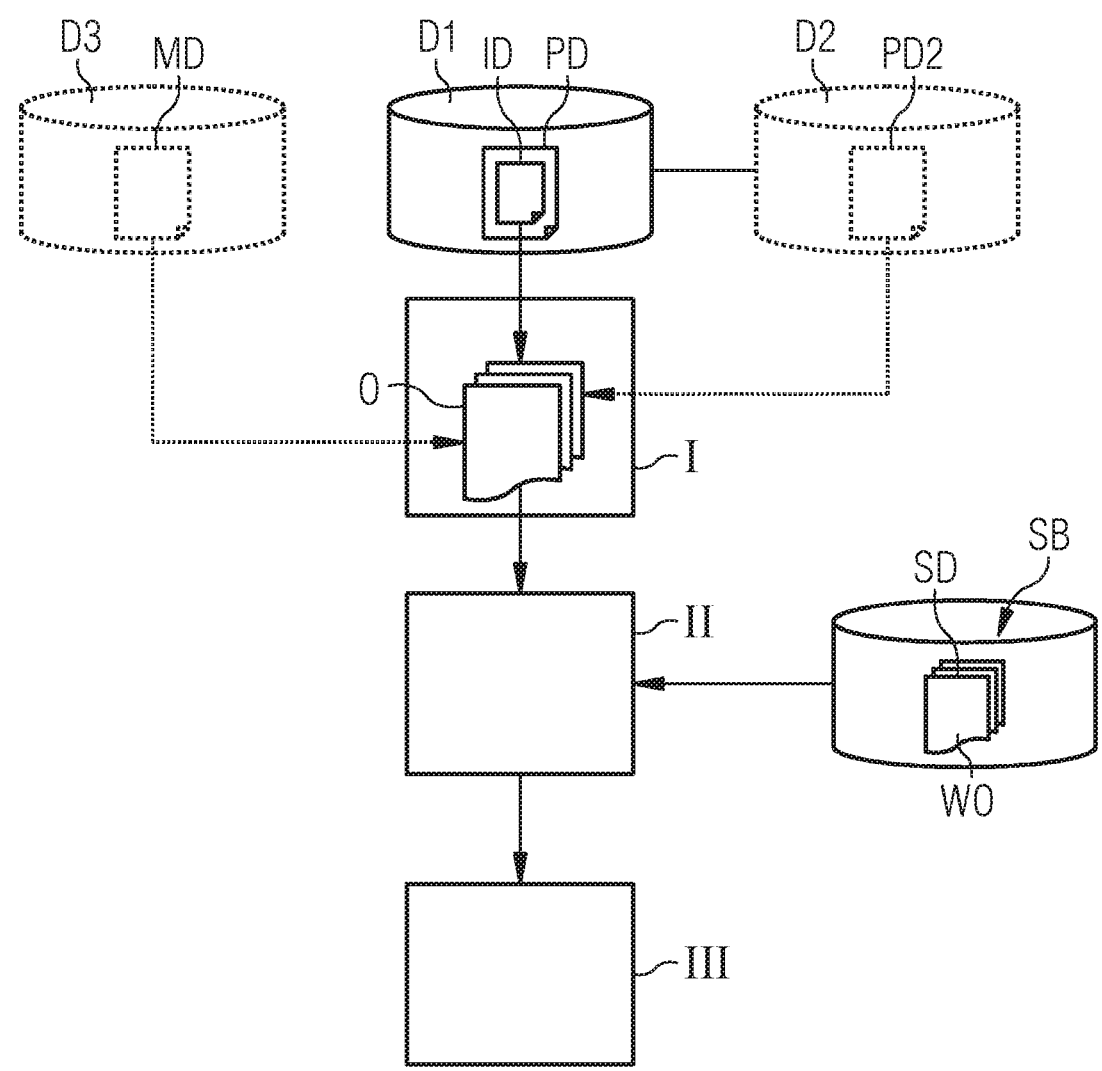
FIG. 1 shows a block diagram for clarifying a possible sequence of a method according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of a method according to the invention for controlling a medical imaging system, in particular for automatically determining control commands for such a system, comprises:

Providing a Data Record for a Patient.

This data record, which can also be referred to as a "patient data record", comprises indication data in this context. This indication data is data regarding a medical indication, which relates to this patient, or a disease pattern which a reporting physician deems probable for said patient. The indication data may also already contain a procedure to be carried out, e.g. from a radiology information system ("RIS") or what is known as a Modality Worklist, in which RIS terminology is mapped to DICOM attributes (DICOM=Digital Imaging and Communications in Medicine).

Transforming the Indication Data into an Ontology.

Such a transformation is also referred to as "mapping", and according to the invention at least relates to indication data, wherein depending on the application other data may also be mapped into the ontology. The ontology in question is an ontology in the sense of information technology. It can also be referred to as an "indication ontology".

In information technology, i.e. in the context of the invention, ontologies are terms, formulated into words and formally arranged, or numerical references to medical data items and the relationships existing between them in the medical subject area. They are used in order to make textual information accessible to a computer apparatus in a digitalized and formal format. Ontologies contain inference and integrity rules, i.e. rules relating to conclusions and ensuring the validity thereof. An ontology thus represents a network of information with logical relationships. In this context, it would also be possible to speak of an explicit formal specification of a conceptualization (concept formation). Ontologies possess a high level of semantic expressivity, whereby they are also able to represent complex data models or knowledge representations.

The ontology thus has a predefined structure and in addition to the indication data can also contain general, standardized knowledge, such as RadLex for example. The RadLex ontology was specified by the "Radiological Society of North America" (RSNA), a union of radiologists, medical physicists and further medical scholars from 136 states, and represents an often-used standard. The aim of using such an ontology is to transform (to "map") text-based prior knowledge regarding the patient, which at least comprises the textually configured indication data, onto the standardized knowledge representation. For the given patient, in particular an instance of this ontology with patient-specific values is generated.

By mapping the indication data into the ontology, the indication data is made directly accessible to a computer apparatus, so that it can process and use the indication data as part of a semantic logic.

The mapping of the indication data into the ontology can take place, for example by semantic analysis, in particular comprising the comparison of text components. The mapping can also, however, take place by converting the diagnostic findings data or by direct interpretation of the diagnostic findings data for a further processing by means of an interpreter. In this framework, the RadLex standard or RadLex Playbook is preferred. This is an expansion of the RadLex ontology and contains a standard lexicon for radiological terminology and references for method steps. One possibility is the "suspected diagnosis" ("admitting diagnosis"), i.e. the diagnosis which is the key factor for whether a CT examination is requested. As a rule, this is a free text composed by a physician, which initially must be mapped onto an ontology in order to be "understood" by a computer system. The admitting diagnosis may read "suspected heart attack", for example.

Optionally, ICD-10 codes can be used to describe the preliminary diagnosis, which contain a formal definition of the clinical relationship or context, wherein a preliminary diagnosis could be an ICD-10-CM diagnosis in accordance with code J44.1, for example, such as "Chronic obstructive pulmonary disease (COPD) with (acute) exacerbation".

Medical reports in hospital information systems or radiology information systems ("HIS" or "RIS"), and recently also in syngo.via, are often based on the HL7 CDA standard, which uses clearly defined technologies, such as SNOMED CT or RadLex for example. As a result, existing information and results regarding the patient are already available in a semantically accessible format in this case. Information can be obtained automatically with a patient ID of the present scan from a source system (HIS, RIS, syngo.via). In such a case, the mapping of the indication data into the ontology represents an examination as to whether all of this data is also present in a correct format for the indication ontology.

Providing a Control Data Library.

This control data library comprises control data records, which are preferably present in a symbolic and/or subsymbolic format, i.e. contain system-comprehensible terms or numerical values. Such control data records may be control protocols (routines for controlling a medical imaging system), contrast protocols (routines for controlling the administration of a contrast medium) or even reconstruction protocols (routines for postprocessing the recorded image data) for at least one medical imaging system. In this context, it is possible that the control data library also comprises control data records for a plurality of medical imaging systems. The control data library preferably has the form of an ontology or is an ontology in which the control data records are mapped. This is described in more detail further below.

The control data library thus contains proprietary knowledge which is specific to the controlling of at least one medical imaging system. This is linked to the indication ontology in a subsequent step.

Automatically Determining a Control Data Record.

Here, this control data record is determined from the control data library as a function of the indication data mapped into the ontology. This determination takes place by means of an inference (logical conclusions) and/or numerical modeling. With regard to this invention, an inference in the sense of information technology-related semantics is of course assumed. In connection with ontologies, the technical functional mechanisms of an inference are known. In an inference, terms of the ontology (indication ontology) and the control data library are correlated and logical conclusions are derived in order to determine the suitable control data record.

In numerical modeling, the determination takes place by numerical means. Numerical models may be results of a machine learning method or statistical analyses, for example. Thus it is possible to derive from a large quantity of indication data and respective associated scan protocols, statistical or "machine learning"-based classification models specified from the clinical routine, for example. For given indication data, these models output numerical probabilities for control data records. In addition, if a "contrast medium allergy" were to be identified from the semantic indication data, an elective or emergency premedication would be recommended as part of the protocol via logical conclusions on the basis of conceptual ontology knowledge in the control data library.

Controlling the Medical Imaging System.

Here, the medical imaging system is controlled with the determined control data record. In this context, image data is generally recorded by means of the system based on the control data in the control data record, which image data can be further processed or directly examined.

The method sequence is illustrated hereinafter on the basis of an example:

During an examination of a patient, a physician makes the diagnosis "suspected heart attack". This text, which is input into the system, is mapped into an ontology as part of the examination. In a very simple case, this can take place by the individual words of the text being analyzed and compared with terms specified in this ontology. In this ontology, the term "heart attack" could then be linked with an indication ("INDICATION: HEART ATTACK", wherein the character string "HEART ATTACK" is a character string known to the system). In RadLex Playbook, a certain control record for a CT would be linked with the indication "HEART ATTACK", wherein the specific characteristics of the CT system used in the medical facility in question would be taken into consideration in the control data record. The inference would then be that as a result of the indication "HEART ATTACK" a control data record linked with said character string would be selected for the CT system used. This control data record could still be altered as a result of additional numerical data, or the selection of the control data record could be influenced by numerical data. For example, the dose for measuring could be adapted to the age of the patient (e.g. child protocol), wherein the age is present as a numerical value. Thus, it is possible for both semantic terms to be evaluated, and also numerical values to enter into the selection or configuration of the control data record via a function.

A control facility according to at least one embodiment of the invention for controlling a medical imaging system, in particular in accordance with the method according to the invention, comprises the following components:

An interface for providing a data record of a patient. As has already been stated above, this patient data record comprises the necessary indication data.

An interface and/or a database for providing a control data library comprising control data records for at least one medical imaging system. In this context, the control data library can be present directly in a data memory of the control apparatus, i.e. in said database, or in an external database, wherein said interface is required for access to said database.

A transfer unit, which is configured for transferring at least the indication data into an (indication) ontology.

A determination unit, which is configured for determining a control data record from the control data library as a function of the indication data mapped into the ontology. Here, the determination unit is embodied to perform the determination by means of a semantic inference and/or a numerical modeling.

The medical imaging system according to at least one embodiment of the invention comprises a control facility according to an embodiment of the invention.

A majority of the aforementioned components of the system may be realized entirely or partially in the form of software modules in a processor of a corresponding control facility. A realization largely through software has the advantage that even conventionally used infrastructure can easily be upgraded by a software update in order to operate in the manner according to the invention. The object is therefore also achieved by a corresponding computer program product with a computer program which can be loaded directly into a memory facility of a control facility of a medical imaging system, having program portions in order to carry out all the steps of the method according to the invention when the program is executed in the control facility. Such a computer program product can comprise, in addition to the computer program, additional components, if relevant, such as for example, documentation or additional components including hardware components, for example, hardware keys (dongles, etc.) in order to use the software.

A computer-readable medium is also preferred in at least one embodiment of the invention, on which program portions that can be read in and executed by a computer unit are stored, in order to carry out all the steps of the method according to an embodiment of the invention when the program portions are executed by the computer unit.

Further, particularly advantageous embodiments and further developments of the invention result from the dependent claims and the description which follows. In this case, the features relating to embodiments of one category may also be used to characterize embodiments of another category. For example, the control facility according to the invention can also be developed similarly to the dependent method claims or parts of the description, wherein the same also applies vice versa for the method claims. It is also possible in particular for individual features of different example embodiments or variants to be combined to form new example embodiments or variants.

Preferably, the control data library comprises control data records for at least two medical imaging systems. This has the advantage for a medical facility that the control data records for a plurality of or all medical imaging devices of a medical facility can be stored in a single control data library. Before the automatic determination of a control data record, however, a manual or optionally also partially automatic selection of a medical imaging system should then advantageously also take place, with which a recording of regions of the body of the patient should be performed. In this case, the control facility preferably comprises an input unit for selecting a medical imaging system, with which a recording should take place.

Thus, a selection of the suitable medical imaging system can be carried out before, during or after the provision of the indication data, and the subsequent control for the selected medical imaging system can take place with the control data record determined for this system.

Preferably, in addition to the indication data, further data of the patient is mapped onto the (indication) ontology. One or more of the following items of data are preferred in this context:

a) Further data in the data record of the patient, in particular data from the group consisting of age, weight, height, ethnicity, gender.

b) Further data from a patient group, e.g. average body mass, typical disease patterns, medical image data.

Preferably, the (indication) ontology comprises additional medical data from the group: Data of a lexical corpus, which can be retrieved in particular from a hospital information system and/or a radiology information system ("HIS" or "RIS"), previous medical history, pre-existing conditions, general state of health, e.g. from HIS/RIS, syngo.via, contrast protocols, information regarding administered contrast agent or scan protocols, e.g. CT or MRI protocols of previous scans and, as required, also reconstructions. The scan protocols may be present in the form of a DICOM header of an image or an independent DICOM file, for example.

Preferably, the control data library comprises data in the RadLex Playbook standard and would thus represent or comprise an ontology, as has already been stated above. This data is preferably based on a semantic scan protocol created in the past and/or current or previous examinations of the patient or a patient group.

RadLex Playbook comprises semantically defined (CT) scan protocols. These scan protocols contain standardized, directly accessible semantic information regarding imaging examinations. In the event that such information can only be obtained as text, reference ontologies such as RadLex or SNOMED CT for example are preferably used for parsing such texts into semantic, that is to say computer-comprehensible information.

Preferably, in order to determine the control data record, a modeling workflow ontology is used, in particular in the OWL standard. Here, this workflow ontology models steps in the scanning procedure, necessary input and output information and available control data for the control data records, such as scan protocols, which contain the totality of scan knowledge for example. In this context, the workflow ontology is constantly expanded or updated with information regarding medical requirements or new control data for the control data record.

The "scan knowledge" comprises the specific knowledge regarding a particular device, e.g. which protocol is used with which parameterization for which examination, which energy is set for imaging in which case or which other settings are carried out on the medical system. The knowledge regarding the controlling of a CT system or a group of CT systems is thus generally contained in the workflow ontology, and a series of control data records for various imaging measurements.

Preferably, the inference or the numerical modeling makes use of the fact that the logical relationships of the data of the patient data record and the control data library has to match the indication data, and only the data which matches the indication data is called upon for the determination. Here, the term "match" relates to a specification within the ontology, i.e. a preset allocation of terms or semantic objects. For example, examinations relating to a broken leg are not taken into consideration during a medical indication regarding heart disease.

Alternatively or in addition, the inference or the numerical modeling makes use of numerical information of the patient or the patient group, in order to obtain optimal parameters for the patient, preferably by means of machine learning procedures such as "deep learning", for example. For example, the selection of the control data record is influenced or the control data record is adapted due to the weight, the height or the age of the patient, wherein this data is present as numerical values. This may take place using simple mathematic functions, for example.

Preferably, after the controlling of the selected medical imaging system and a recording of an image data record by the medical imaging system, the image data record is automatically or semi-automatically reconstructed and/or graphically post-processed, in particularly based on the determined control data record. To this end, a modeling workflow ontology is used for image reconstruction, which is particularly preferably constantly expanded or updated with information regarding reconstruction protocols. Preferably, the image reconstruction is part of the workflow ontology described further above, which is used for selecting the control data record. To this end, this preferably has a modular design. The image reconstruction may also already be a direct part of a control data record.

In order to enable an optimal evaluation of image data records, which have been recorded in order to examine a patient, on the part of a reporting physician, so that they are capable of making a reliable diagnosis in a simple manner, it is preferred that the images recorded by the medical imaging system are made available to the reporting physician according to the indication data. To this end, the images have to undergo a specific reconstruction, optionally a different reconstruction in each case, and obtain a compilation as a function of the indication data.

In accordance with an example embodiment development of the method, after the controlling of the selected medical imaging system and a recording of an image data record by the medical imaging system, said image data record is automatically prepared for display to a reporting physician by a measurement data representation algorithm. This measurement data representation algorithm can be determined from a representation library automatically, based on the indication data and/or the control data record. To this end, a preferred control facility comprises a database with said representation library or an interface for accessing such a database.

Preferably, further data is additionally allocated to the control data record during or after its determination, in particular based on the (indication) ontology containing data of the patient, a patient group and/or a lexical corpus, wherein this further data supplies the measurement data representation algorithm with information for representing the measurement data.

Preferably, in addition to the image data record, the measurement data representation algorithm also prepares data of the data record of the patient, i.e. not only the indication data, but rather further data relating to the patient, and in particular likewise data of a lexical database, automatically for display to a reporting physician.

One advantage of at least one embodiment of the invention is that an automatic, case-specific image recording and reconstruction is made possible, in which in particular the clinical history can be recorded or taken into consideration therein.

In this manner, it is possible to make optimal images automatically available to a radiologist tasked with the examination.

At least one embodiment of the invention is particularly applicable for what are known as automation-compatible and PACS-compatible scenarios, which have the aim of enabling fault-tolerant image recordings and evaluations.

Figure 2:
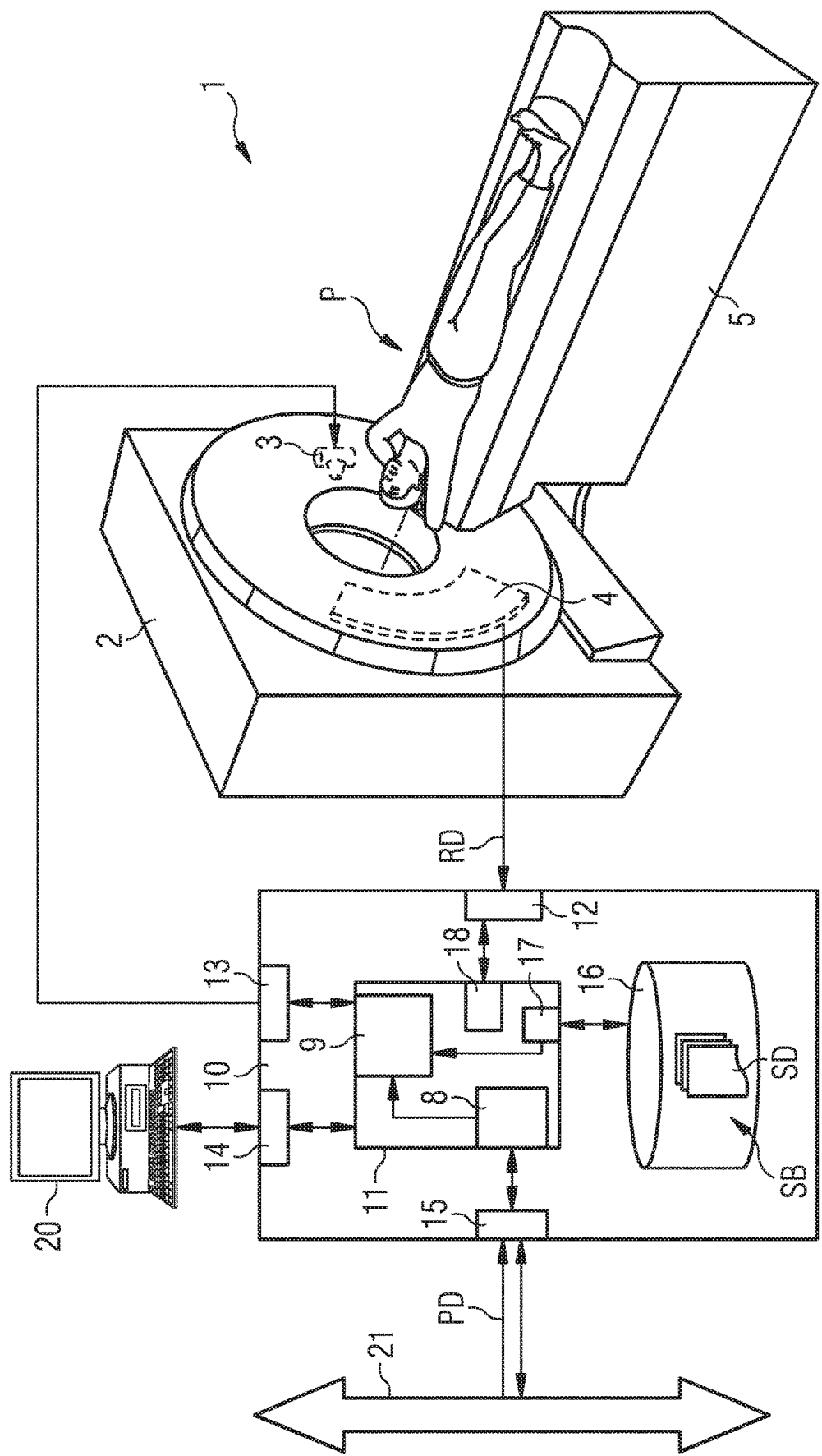
FIG. 2 shows a schematic representation of a preferred control facility.

FIG. 1 shows a block diagram for clarifying a possible sequence of a method according to the invention for controlling a medical imaging system 1, as is depicted in FIG. 2 for example.

Firstly, a patient data record PD containing indication data ID is provided by a database D1. In this case, the indication data ID is mapped into an (indication) ontology O in step I. Depending on the application, the patient data PD could also be mapped into the ontology O on a supplementary basis.

Two further databases D2, D3 are indicated with dotted lines, the data of which could optionally likewise be mapped into the ontology O. The right database D2 contains further patient data PD2, e.g. diagnostic findings data from a further physician, the left database D3 contains additional medical data MD, such as image data recorded in the past for example.

In addition to mapping the indication data ID and, if necessary, further data into the ontology O in step I, there follows a provision of a control data library SB comprising control data records SD, in particular in the form of a workflow ontology WO. This control data library SD may indeed involve an independent database, the data of which is the control data records SD. In the following, however, it is simply assumed that the control data library SB is present as a number of control data records SD in a database.

In step II, there follows an automatic determination of a control data record SD from the control data library SB as a function of the indication data ID mapped into the (indication) ontology O. This takes place by means of a semantic inference and/or numerical modeling.

In step II, the medical imaging system 1 is then controlled with the determined control data record SD.

FIG. 2 shows a schematic representation of a preferred control facility 10 for controlling a medical imaging system 1, which here—merely as an example—is a computed tomography system 1. Represented in the control facility 10 are only those components which are significant or useful for explaining the invention, since the design and the functionality of a computed tomography system 1 are known to the person skilled in the art and do not need to be explained in more detail.

The computed tomography system 1 has a scanner 2 with a gantry in a conventional manner, in which an x-ray source 3 rotates, which in each case irradiates a patient who is slid into a measuring space of the gantry by means of a couch 5, so that the radiation strikes a detector 4 lying opposite the x-ray source 3 in each case.

Here, a core component of the control facility 10 is a processor 11, on which various components are realized in the form of software modules. Furthermore, the control facility 10 has a terminal interface 14, to which a terminal 20 is connected, via which an operator can operate the control facility 10 and thus the computed tomography system 1. A further interface 15 is a network interface for connecting to a data bus 21, in order thus to make a connection to an RIS or PACS. In this case the indication data ID and, if necessary, further data of the patient data record PD or other databases are provided via this data bus 21.

Via a control interface 13, the scanner 2 can be actuated by the control facility 10, i.e. the rotational speed of the gantry, the displacement of the couch 5 and the x-ray source 3 itself are controlled for example. The raw data RD is read out from the detector 4 via an acquisition interface 12. Furthermore, the control facility 10 has a memory unit 16. In the case shown here, the memory unit 16 comprises the complete control data library SB with the individual control data records SD. The memory unit 16 is connected to the processor 11 via the interface 17. Theoretically, it would alternatively be possible to also gain access to a control data library SB via a network or the data bus 21. The control data library SB could also be implemented directly in the memory area of the processor 11.

A further component on the processor 11 is a transfer unit 8, which is designed to transfer the indication data ID and, if necessary, also other data into an ontology O.

Furthermore, a determination unit 9 is present on the processor 11, which is designed for determining a control data record SD from the control data library SB as a function of the indication data ID mapped into the ontology O, by means of a semantic inference and/or numerical modeling.

A further component on the processor 11 is an image data reconstruction unit 18, with which the desired image data is reconstructed from the raw data RD obtained via the data acquisition interface 12. This may then be available to the preferred embodiment described below.

FIG. 3 shows a block diagram for clarifying the sequence of a preferred embodiment of the method according to the invention. As in FIG. 1, indication data ID and, if necessary, further patient data PD or the data mentioned as part of the explanations related to FIG. 1 are mapped into an ontology O in a step I.

In a subsequent step II, as likewise described in FIG. 1, a control data record SD is determined from a control data library SB.

In step III, a medical imaging system 1 is controlled, which in step IV results in the recording of raw data RD of an image.

This raw data RD is then transferred to an image reconstruction unit 18, which in step V carries out a reconstruction of the raw data RD according to the specifications of the control data record SD. This results in image data which a reporting physician would be able to understand.

In step VI, this image data is processed by a measurement data representation algorithm MA, which is selected based on the indication data ID, and a presentation is created which may also contain further data, if necessary. Ideally, the images are represented according to the indication data ID in the best manner for the optimal appraisal for the specific disease pattern.

In the final step VII, the images and, if necessary, additional data which are processed in such a manner are output for a reporting physician, for example printed out and/or shown on a monitor.

Finally it should be noted again that the above method, as described in detail, and the illustrated control facility 10 are only example embodiments which can be modified by the person skilled in the art in a wide variety of ways without departing from the scope of the invention. Furthermore, the use of the indefinite article "a" or "an" does not preclude the relevant features also being present plurally. Likewise the terms "unit" or "module" do not mean that these cannot consist of a number of interacting components, which can in some instances also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for controlling a medical imaging system, comprising:
   providing a data record for a patient, the data record including indication data;
   mapping at least the indication data into an ontology such that the indication data is made directly accessible to a computer apparatus by semantic analysis comprising comparison of text components as part of a semantic logic to generate patient-specific values;
   providing a control data library including control data records for at least one medical imaging system;
   automatically determining a control data record from the control data library as a function of the indication data mapped into the ontology, via a semantic inference;
   controlling the medical imaging system with the control data record automatically determined; and
   automatically preparing an image data record via a measurement data representation algorithm after the controlling of the medical imaging system and after a recording of the image data record by the medical imaging system, and displaying the automatically prepared image data record, wherein the measurement data representation algorithm is determined from a representation library, automatically, based upon at least one of the indication data and the control data record.

2. The method of claim 1, wherein the control data library includes control data records for at least two medical imaging systems, the method further comprising:
   selecting, before the automatic determining of the control data record, the medical imaging system from the at least two medical imaging systems, and
   wherein a recording of regions of a body of the patient is performed.

3. The method of claim 1, wherein the indication data includes further data of the patient, and wherein the further data of the patient is also mapped onto the ontology during the mapping.

4. The method of claim 1, wherein the ontology includes additional medical data selected from the group consisting of previous medical history, pre-existing conditions, general state of health, scan protocols, contrast protocols and further data from a lexical corpus.

5. The method of claim 1, wherein the control data library includes data in a RadLex Playbook standard, and wherein the data in the RadLex Playbook standard is based on at least one of a previous scan protocol and at least one current or previous examination of the patient or a patient group.

6. The method of claim 1, wherein the automatically determining the control data record includes use of a modeling workflow ontology, wherein the workflow ontology models steps of a scan procedure, necessary input and output information and available control data, including a totality of scan knowledge.

7. The method of claim 1, wherein the semantic inference makes use of at least one of
   logical relationships, of the data of the data record of the patient and the control data library, to match the indication data, and wherein only data which matches the indication data is called upon for the determining, and
   numerical information of the patient or a patient group, via machine learning procedures.

8. The method of claim 1, wherein after the controlling of the medical imaging system and after the recording of the image data record by the medical imaging system, the image data record is automatically or semi-automatically at least one of reconstructed and graphically post-processed.

9. The method of claim 1, wherein further data is additionally allocated to the control data record during or after the determining, the further data supplying the measurement data representation algorithm with information for representing the measurement data.

10. The method of claim 1, wherein, in addition to the image data record, at least one of data of the data record of the patient and data of a lexical database, are automatically prepared via the measurement data representation algorithm for display to a reporting physician.

11. A system for controlling a medical imaging system, comprising:

an interface to provide a data record of a patient, the data record including indication data;

at least one of an interface and a database, to provide a control data library including control data records for at least one medical imaging system;

a processor configured to map at least the indication data into an ontology such that the indication data is made directly accessible to a computer apparatus by semantic analysis comprising comparison of text components as part of a semantic logic to generate patient-specific values, determine a control data record from the control data library as a function of the indication data mapped into the ontology, via a semantic inference control the medical imaging system with the determined control data record, and prepare an image data record via a measurement data representation algorithm after the controlling of the medical imaging system and after a recording of the image data record by the medical imaging system, and display the prepared image data record, wherein the measurement data representation algorithm is determined from a representation library, automatically, based upon at least one of the indication data and the control data record.

12. The system of claim 11 further comprising a medical imaging device.

13. A non-transitory computer program product, comprising a computer program, directly loadable into a memory store of a control facility of a medical imaging system, including program portions configured to carry the method of claim 1 when the computer program of the non-transitory computer program product is executed by a computer of the medical imaging system.

14. A non-transitory computer-readable medium storing program portions, readable in and executable by a computer, configured to carry out the method of claim 1 when the program portions of the non-transitory computer-readable medium are executed by the computer.

15. The method of claim 2, wherein in addition to indication data, the indication data includes further data of the patient, and wherein the further data of the patient is also mapped onto the ontology during the mapping.

16. The method of claim 2, wherein the indication data includes further data of the patient, and wherein the further data of the patient is also mapped onto the ontology during the mapping.

17. The method of claim 3, wherein the further data includes at least one of
further data in the data record of the patient, and
further data of a patient group.

18. The method of claim 17, wherein the further data in the data record of the patient includes data selected from the group consisting of age, weight, height, ethnicity, gender.

19. The method of claim 17, wherein the further data of the patient group is retrievable from at least one of a hospital information system and a radiology information system.

20. The method of claim 6, wherein the modeling workflow ontology is constantly expanded or updated with information regarding medical requirements or new control data.

21. The method of claim 8, wherein the modeling workflow ontology is used for the image reconstruction.

22. The method of claim 21, wherein the modeling workflow ontology is constantly expanded or updated with information regarding reconstruction protocols.

23. The method of claim 9, wherein the further data is additionally allocated to the control data record during or after the determining based on at least one of ontology containing data of the patient, a patient group and a lexical corpus.

24. A non-transitory computer program product, comprising a computer program, directly loadable into a memory store of a control facility of a medical imaging system, including program portions configured to carry the method of claim 2 when the computer program of the non-transitory computer program product is executed by a computer of the medical imaging system.

25. A non-transitory computer-readable medium storing program portions, readable in and executable by a computer, configured to carry out the method of claim 2 when the program portions of the non-transitory computer-readable medium are executed by the computer.

26. The method of claim 1, wherein the automatic determining of the control data record via the semantic inference is based on a preset mapping of semantic objects within the ontology.

* * * * *